United States Patent [19]

Pernot

[11] 4,266,934
[45] May 12, 1981

[54] DENTAL HANDPIECE WITH FLUID DELIVERY CONTROL

[75] Inventor: Jacques Pernot, Besancon, France

[73] Assignee: Micro-Mega, S.A., Besancon, France

[21] Appl. No.: 73,501

[22] Filed: Sep. 7, 1979

[30] Foreign Application Priority Data

Sep. 11, 1978 [FR] France .................. 78 26633

[51] Int. Cl.³ .............................................. A61C 1/00
[52] U.S. Cl. ........................................ 433/85; 433/100
[58] Field of Search ................... 433/100, 85, 84, 80, 433/99, 98; 239/415, 414; 137/625.41, 625.46, 602

[56] References Cited

U.S. PATENT DOCUMENTS

| Re. 25,130 | 2/1962 | Madsen, Jr. | 433/98 |
| 1,642,623 | 9/1927 | Niven | 137/625.41 |
| 1,989,468 | 1/1935 | Spencer | 239/414 |
| 2,639,678 | 5/1953 | Martin | 137/625.41 |
| 3,115,896 | 12/1963 | Roberts et al. | 137/625.41 |
| 4,007,529 | 2/1977 | Fleer | 433/84 |
| 4,146,055 | 3/1979 | Ryder et al. | 137/625.41 |

FOREIGN PATENT DOCUMENTS

| 635108 | 1/1962 | Canada | 433/100 |
| 649386 | 6/1929 | Fed. Rep. of Germany | 137/625.41 |
| 1274789 | 8/1968 | Fed. Rep. of Germany | 433/100 |
| 2750451 | 8/1978 | Fed. Rep. of Germany | 433/85 |

Primary Examiner—Gene Mancene
Assistant Examiner—John J. Wilson
Attorney, Agent, or Firm—Robert E. Burns; Emmanuel J. Lobato; Bruce L. Adams

[57] ABSTRACT

This dental handpiece comprises means for controlling the delivery of compressed air and water to an outlet conduit leading to the head of the handpiece. The water and air supply conduits from the motor open each into a circular groove formed in the inner periphery of a socket easily fitted on the tool holder retaining end of the motor. Radial ports formed in the socket open on the one hand into the grooves, respectively, and on the other hand into an annular chamber formed between the socket and the handpiece body, the outlet conduit extending from this chamber. A rotary ring accessible from outside the handpiece body is provided with a pair of seals off-set axially and angularly to each other and so arranged that in two end positions of the ring one of the two supply conduits is closed while the other conduit is open, and that in an intermediate position both conduits are open.

5 Claims, 5 Drawing Figures

DENTAL HANDPIECE WITH FLUID DELIVERY CONTROL

FIELD OF THE INVENTION

The invention relates to a dental handpiece provided with means for controlling the delivery of fluids to the tool holder, which comprises an air supply conduit and a water supply conduit from the motor, and an outlet conduit leading to the handpiece head.

DESCRIPTION OF THE PRIOR ART

Dental handpiece provided with internal or partly internal conduits for delivering compressed air and water for watering the tool or cleaning the burred tooth cavities are already known in the art.

Various solutions have already been proposed for solving the problem of connecting these conduits to the head or told holder and to the body of the handpiece. Thus, in the French Pat. No. 2,235,670, this problem is solved by providing a water supply conduit from the motor which opens at the periphery of the endmost motor portion into an inner circular groove formed in the handpiece between two seals of the retaining socket, said groove communicating with a small tube leading to the head of the handpiece.

According to another known device, two inlets are provided, i.e. an air inlet and a water inlet, connected via two separate outlet conduits to the head of the handpiece. With this double conduit it is possible to direct towards the bur either air alone for cleaning the tooth cavity or water alone, or a mixture of air and water. However, this device requires special control means associated with the treadle controlling the motor operation, namely solenoid-valves.

It is the essential object of this invention to avoid this inconvenience.

SUMMARY OF THE INVENTION

To this end, the handpiece according to this invention is characterised in that the water and air supply conduits open each into a separate circular groove formed at the inner periphery of a socket which is an easy fit on the motor receiving end, said socket having formed therein a pair of radial holes off-set both axially and angularly, said holes opening on the one hand into said grooves and on the other hand into an annular chamber formed between said socket and the body of the handpiece, the outlet conduit leading from said chamber to the tool holder and that a rotary ring adapted to be easily actuated from outside is mounted in said chamber and provided in its peripheral wall with a pair of seals off-set in the axial direction by the same distance as said socket holes and so shaped that in a first limit position of said ring the first seal closes the water supply port while the second seal uncovers the air supply port, in a second limit position said first seal uncovers said water supply port while said second seal closes the air supply port, and in an intermediate position both seals uncover the air and water supply ports.

DESCRIPTION OF THE PREFERRED EMBODIMENT

Figure 5:
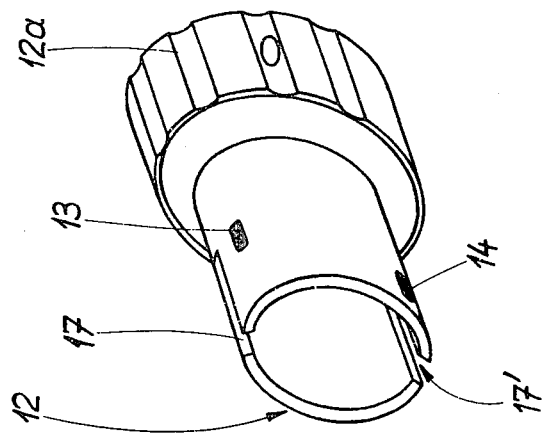
FIG. 5 is a perspective view of the ring.

Screwed in the body 1 of the dental handpiece is a socket 2 adapted to be easily fitted to the retaining end 3' of motor 3.

A water supply conduit 4 and an air supply conduit 5 from the motor 3 open at the outer periphery of the motor end 3' into circular grooves 6 and 7, respectively, formed in the inner wall of socket 2. Three O-rings 8 fitted in corresponding grooves formed on the retaining end 3' of motor 3 seal the joint between the motor 3 and the handpiece 1.

The wall of socket 2 has formed therethrough a pair of radial ports 9,10 opening on the one hand into grooves 6,7 respectively and on the other hand into a chamber 11 formed between the socket 2 and the handpiece body 1, the outlet conduit 18 communicating directly with this chamber 11 and being connected to the head of the handpiece. The ports 9 and 10 are off-set angularly to each other. In the form of embodiment illustrated in the drawing, the ports 9 and 10 are diametrally opposed. A ring 12 is rotatably mounted on the end of body 1 in said chamber 11. This ring 12 comprises a rear extension 12a of greater diameter, formed with a knurled or similar outer surface to facilitate its rotation by the practitioner. A pair of rectangular-sectioned seals 13 and 14 are fitted in adequate holes formed through the peripheral wall of ring 12 so that, according to the position in which the ring 12 is set, the water port 9 and/or the air port 10 can be closed at will.

Figure 2:
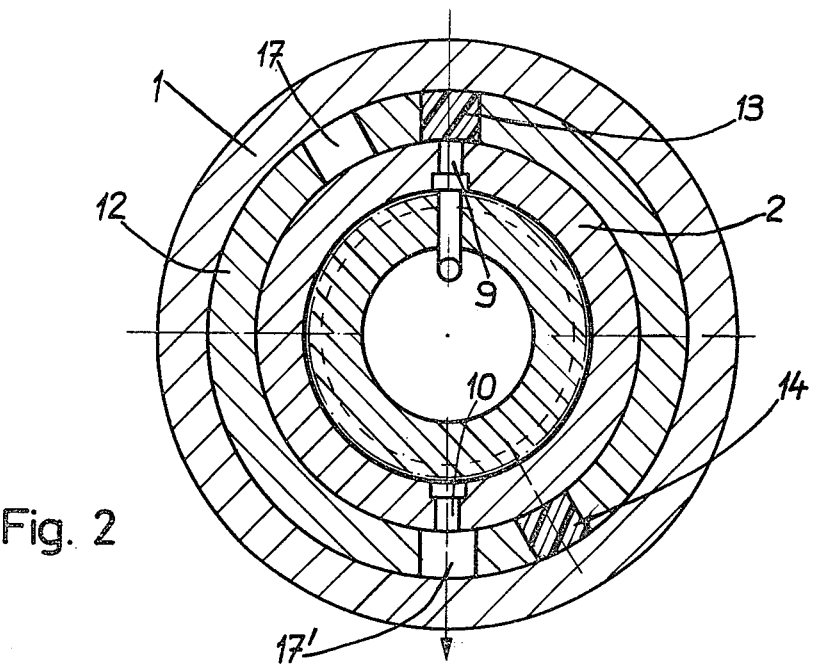
FIG. 2 is a section taken along the line II—II of FIG. 1.
Figure 3:
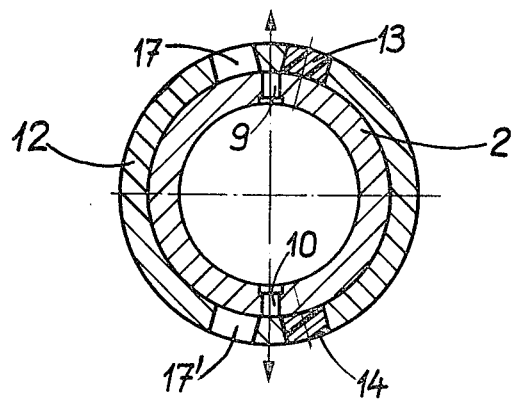
FIGS. 3 and 4 are diagrammatic cross sections showing two other possible positions of the rotary ring.
Figure 4:
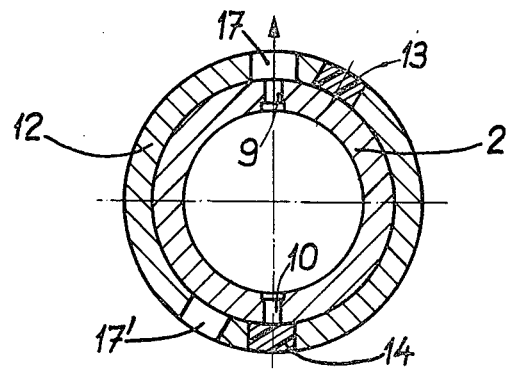

These seals 13 and 14 are therefore off-set in the axial direction to the same extent as the air and water supply ports 9 and 10. Moreover, as illustrated in FIGS. 2, 3 and 4, the rectangular seals 13 and 14 are off-set angularly by an angle smaller than the angle of shift between ports 9 and 10, therefore, in the form of embodiment illustrated, by an angle of less than 180°. The ring 12 further comprises a pair of radial slots 17,17' diametrally opposed to the locations of seals 14 and 13, respectively, as clearly shown in FIG. 5.

A pair of diametrally opposed radial pins 15 are tightly fitted in holes formed through the larger portion of ring 12 for engagement with the ends of a slot 16 formed in socket 2 in order to define two limit positions of ring 12. Alternatively, spring-loaded balls could be substituted for these pins 15, the balls being adapted to engage one of three cavities formed in the socket, so that one intermediate position may be obtained in addition to the two limit positions.

A pair of O-rings 19 seal the joints between body 1, socket 2 and ring 12.

Figure 1:
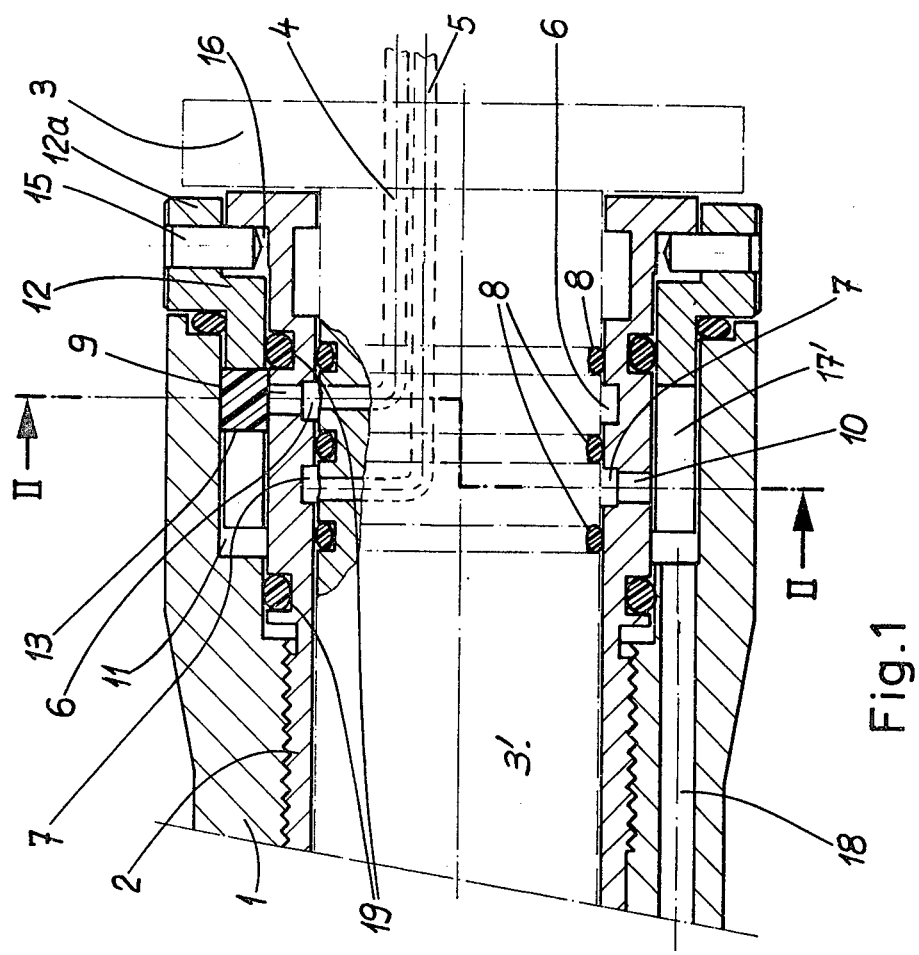
FIG. 1 is a fragmentary axial section showing the end of the handpiece with the rotary ring set in a first limit position, according to a typical form of embodiment of the invention.

The above-described device operates as follows:

Assuming the ring 12 to be in the first limit position shown in FIGS. 1 and 2, the seal 13 will prevent the water from flowing through the radial port 9 and the seal 14 is spaced from the air outlet port 10, so that the air flowing in conduit 5 can escape into chamber 11 (this flow being facilitated by the radial slot 17' of ring 12), and then via outlet conduit 18 to the head of the handpiece.

Now when the ring 12 is set in the intermediate position shown in FIG. 3, the air and water outlet ports 10 and 9, respectively, are uncovered by seals 13 and 14, so that air and water can be mixed together in chamber 11 before escaping through the outlet conduit 18 to the head of the handpiece.

Finally, when the ring 12 is set in its other limit position shown in FIG. 4, the rectangular seal 13 is moved away from the water outlet port 9 and the seal 14 closes the air outlet port 10, so that water can escape through the slot 17 of ring 12 to chamber 11 and from this chamber via the outlet conduit 18 to the head of the handpiece.

Of course, various modifications and changes may be brought to the specific form of embodiment shown and described herein, without departing from the basic principles of the invention as set forth in the appended claims.

What is claimed is:

1. A dental handpiece provided with means for controlling the delivery of fluids to the tool, which comprises an air supply conduit and a water supply conduit from the motor and an outlet conduit directed to the head of the handpiece, wherein said water and air supply conduits open each into a circular groove, respectively, formed in the inner periphery of a socket which is an easy fit to the retaining end of the motor, said socket having two radial ports formed through its wall, said ports being off-set both axially and angularly, and opening on the one hand into said grooves and on the other hand into an annular chamber formed between said socket and the body of the handpiece, said outlet conduit being connected to said chamber, a rotary ring adapted to be easily rotated from outside being mounted in said chamber and provided in its peripheral wall with a pair of seals off-set axially to the same extent as said ports formed in the socket, said seals being so shaped that in the first limit position of said ring the first seal closes the water supply port while the second seal uncovers the air supply port, in a second limit position said first seal uncovers said water supply port while said other seal closes said air supply port, an intermediate position of said ring causing said seals to free both air and water supply ports.

2. A dental handpiece according to claim 1, wherein said seals are rectangular seals fitting in corresponding holes formed in the peripheral wall of said ring so as to be off-set angularly to each other through an angle smaller than the angle of shift existing between said ports.

3. A dental handpiece according to claim 2, wherein said ring has a pair of axial slots formed therein, each slot being diametrically opposed to the location of said seal.

4. A dental handpiece according to claim 1, wherein said ring is provided with at least one radial pin engaging a slot formed in said socket for defining said two limit positions.

5. A dental handpiece according to claim 1, wherein said ring is provided with at least one spring-loaded ball engageable in cavities formed in said socket for defining the three operative positions of said ring.

* * * * *